(12) United States Patent
Jamison et al.

(10) Patent No.: US 11,525,356 B1
(45) Date of Patent: Dec. 13, 2022

(54) IDENTIFYING TYPES OF CONTAMINATIONS OF DRILLING FLUIDS FOR A DRILLING OPERATION

(71) Applicant: Halliburton Energy Services, Inc., Houston, TX (US)

(72) Inventors: Dale E. Jamison, Humble, TX (US); Sandeep Dileep Kulkarni, Houston, TX (US); Lalit Narayan Mahajan, Fremont, CA (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 17/546,028

(22) Filed: Dec. 8, 2021

(51) Int. Cl.
*E21B 49/00* (2006.01)
*G01N 9/00* (2006.01)
*E21B 49/08* (2006.01)
*G01N 33/28* (2006.01)
*E21B 47/047* (2012.01)

(52) U.S. Cl.
CPC ........ *E21B 49/003* (2013.01); *E21B 49/0875* (2020.05); *G01N 9/00* (2013.01); *G01N 33/2823* (2013.01); *E21B 47/047* (2020.05); *E21B 2200/20* (2020.05)

(58) Field of Classification Search
CPC .. E21B 49/003; E21B 49/0875; E21B 47/047; E21B 2200/20; G01N 9/00; G01N 33/2823

USPC ....................................................... 73/152.04
See application file for complete search history.

(56) References Cited

U.S. PATENT DOCUMENTS

| | | | | |
|---|---|---|---|---|
| 7,081,615 | B2 * | 7/2006 | Betancourt | E21B 47/10 250/255 |
| 2007/0119244 | A1 * | 5/2007 | Goodwin | G01N 33/2823 73/152.28 |
| 2009/0235731 | A1 * | 9/2009 | Zuo | G01N 33/2823 73/152.28 |
| 2013/0312481 | A1 * | 11/2013 | Pelletier | G01V 11/00 73/1.02 |
| 2019/0227048 | A1 * | 7/2019 | Ye | G01N 27/026 |
| 2020/0018739 | A1 * | 1/2020 | Khan | E21B 47/06 |

* cited by examiner

*Primary Examiner* — Marrit Eyassu
(74) *Attorney, Agent, or Firm* — Kilpatrick Townsend & Stockton LLP

(57) ABSTRACT

A system can identify a type of contamination for drilling fluid based on measured fluid properties of the drilling fluid and fluid properties of a reference drilling fluid. A system can measure a first plurality of fluid properties for a drilling fluid sample contaminated from a wellbore drilling operation. A system can select a predicted model in relation to one or more types of contamination by comparing the first plurality of fluid properties and a second plurality of fluid properties measured from a reference fluid sample. A system can analyze the first plurality of fluid properties and a third plurality of fluid properties generated from the predicted model to determine a first type of contamination in the drilling fluid sample.

20 Claims, 5 Drawing Sheets

IDENTIFYING TYPES OF CONTAMINATIONS OF DRILLING FLUIDS FOR A DRILLING OPERATION

TECHNICAL FIELD

The present disclosure relates generally to drilling operations and, more particularly (although not necessarily exclusively), to identifying contamination type of drilling fluid in a drilling operation using one or more measurements.

BACKGROUND

A wellbore can be formed in a subterranean formation for extracting produced hydrocarbon or other suitable material. A drilling operation can be performed from the wellbore. The drilling operation can include or otherwise involve drilling fluid for various purposes, such as lubricating a drilling bit, maintaining wellbore stability, and removing wellbore cuttings. Sometimes, drilling fluid may become contaminated from Brine, oil, or other components in the wellbore, and may be ineffective in serving its purpose.

DETAILED DESCRIPTION

Figure 1:
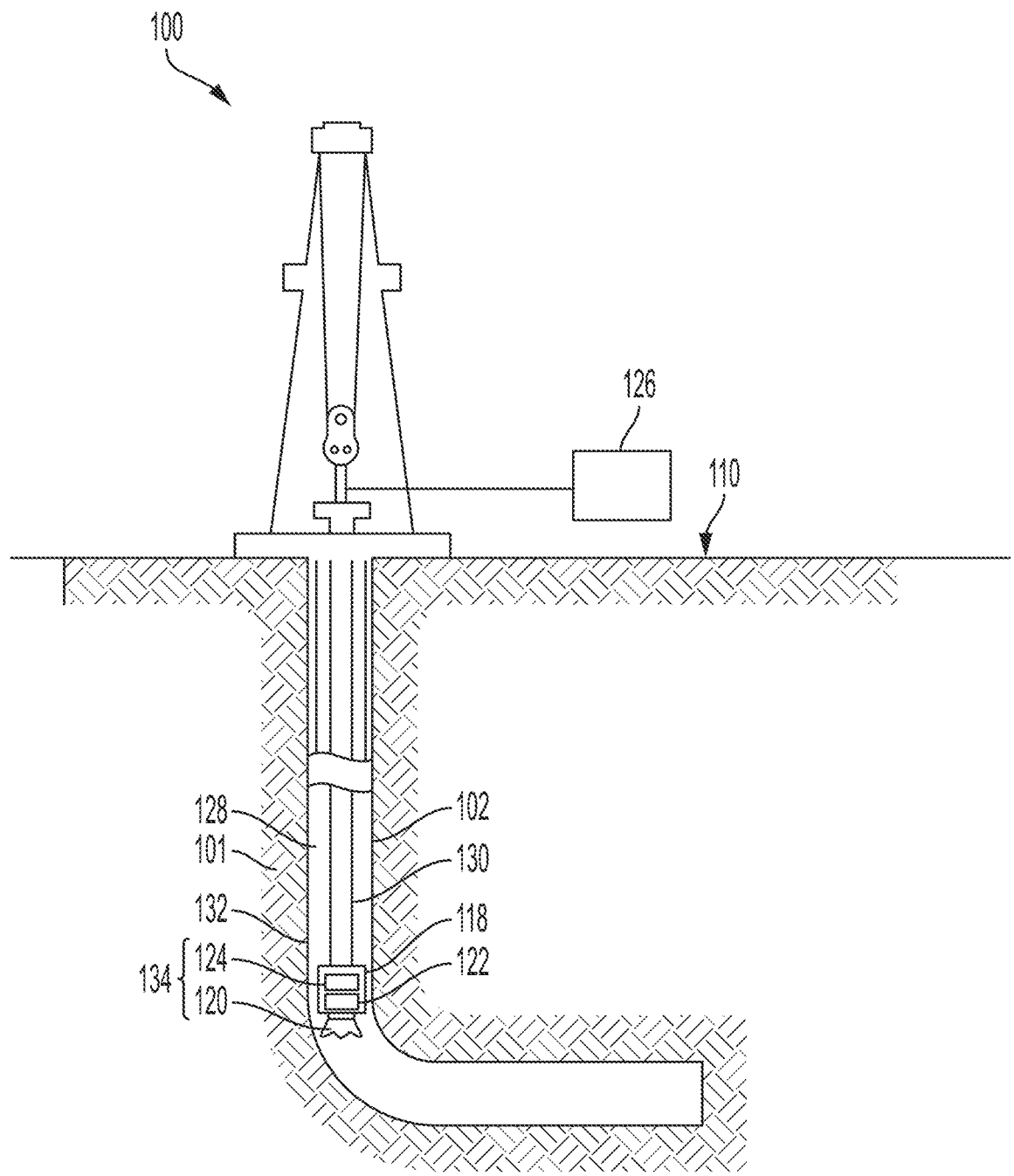
FIG. 1 is a schematic of a drilling system for drilling a wellbore using drilling fluid and includes a drilling fluid analysis system for identifying a type of contamination of drilling fluid according to one example of the present disclosure.

Certain aspects and examples of the present disclosure relate to identifying a type of contamination for drilling fluid based on measured fluid properties of the drilling fluid and fluid properties of a reference drilling fluid. A wellbore may include a drilling system for pumping drilling fluid into the wellbore. The drilling system may measure drilling fluid surrounding a drilling rig or drilling fluid from the subterranean formation. The drilling system may further analyze drilling fluid properties. Examples of fluid properties can include mud weight (MW), thermal conductivity (TC), density, and salinity in drilling fluid. In some examples, contaminated compounds may enter into drilling fluid during the drilling operation. In other examples, drilling fluid may be contaminated from various secures. For example, drilling fluids may be contaminated from subterranean formation materials or thermal degradation of organic compounds in mud. Generally, contamination types of drilling fluid can include oil, Brine, low gravity solid (LGS), high gravity solid (HGS). In some examples, contamination type in drilling fluid can be determined using a reference fluid and reference fluid properties. In order to maintain the drilling performance of the drilling system, measuring drilling fluid properties can be useful to estimate one or more possible contamination types in drilling fluid during the drilling operation.

In some aspects, drilling fluid properties can be manually tested by the American Petroleum Institute (API) procedures. However, the API procedures usually take about 6 to 12 hours to carry out each work on measuring drilling fluid properties that may be considered time-consuming. Yet, the drilling fluid may be changed dramatically during a short period of time. In some examples, contaminated drilling fluid may degrade quality of drilling fluid and lead to unexpected changes in drilling fluid properties. Once the contaminated drilling fluid from the drilling bit entered into the wellbore, dramatic changes in wellbore pressure and temperature may occur. Therefore, timely and accurately measuring drilling fluid properties can be critical to identify contaminations in drilling fluid on a real-time basis and prevent severe issues in the wellbore in advance.

In some examples, drilling fluid can be measured using a non-destructive manner in fluid mud weight (MW) and thermal conductivity (TC). In some examples, a commercially available thermal conductivity probe (e.g., KD-2 pro) can be employed to use in measuring drilling fluid properties, including TC, MW, density, and salinity, in drilling fluid every 5 to 10 minutes.

The above illustrative examples are given to introduce the reader to the general subject matter discussed herein and are not intended to limit the scope of the disclosed concepts. The following sections describe various additional features and examples with reference to the drawings in which like numerals indicate like elements, and directional descriptions are used to describe the illustrative aspects, but, like the illustrative aspects, should not be used to limit the present disclosure.

FIG. 1 is a schematic of a drilling system for drilling a wellbore using drilling fluid and includes a drilling fluid analysis device 126 for identifying a type of contamination of drilling fluid according to one example of the present disclosure. In this example, a drilling rig 100 is depicted for a well, such as an oil or gas well, for extracting fluids from a subterranean formation 101. The drilling rig 100 may be used to create a wellbore 102 from a surface 110 of the subterranean formation 101. The drilling rig 100 may include a well tool or downhole tool 118, and a drill bit 120. The downhole tool 118 can be any tool used to gather information about the wellbore 102. For example, the downhole tool 118 can be a tool used for measuring-while-drilling or logging-while-drilling operations. The downhole tool 118 can include a sensor 122 for collecting wellbore data. Examples of wellbore data can include rate of penetration, weight on bit, standpipe pressure, depth, mud weight, rotations per minute, torque, equivalent circulating density, or other parameters. The downhole tool 118 can also include a transmitter 124 for transmitting data from the sensor 122 to the surface 110. A bottom hole assembly 134 can include the downhole tool 118 and the drill bit 120 for drilling the wellbore 102.

The wellbore 102 is shown as being drilled from the surface 110 and through the subterranean formation 101. As the wellbore 102 is drilled, drilling fluid can be pumped through the drill bit 120 and into the wellbore 102 to enhance drilling operations. As the drilling fluid enters into the wellbore, the drilling fluid circulates back toward the surface 110 through a wellbore annulus 128, which is an area between a drill string 130 and a wall 132 of the wellbore 102. In some examples, shear stress on the subterranean formation 101 may cause a breakout in the subterranean formation 101 surrounding the wellbore 102. Contaminated components from the breakout may enter the drilling fluid. The sensor 122 may collect data, such as fluid properties of drilling fluid 212.

Also included in the schematic diagram is a drilling fluid analysis device 126. The drilling fluid analysis device 126 can be communicatively coupled to the downhole tool 118 and receive real-time information about the drilling operation. The drilling fluid analysis device 126 can determine a type of contamination in drilling fluid using fluid properties of drilling fluid received from the sensor 122. In some examples, the drilling fluid analysis device 126 may determine types of contamination of drilling fluid 222 for the drilling operation in real-time.

Figure 2:
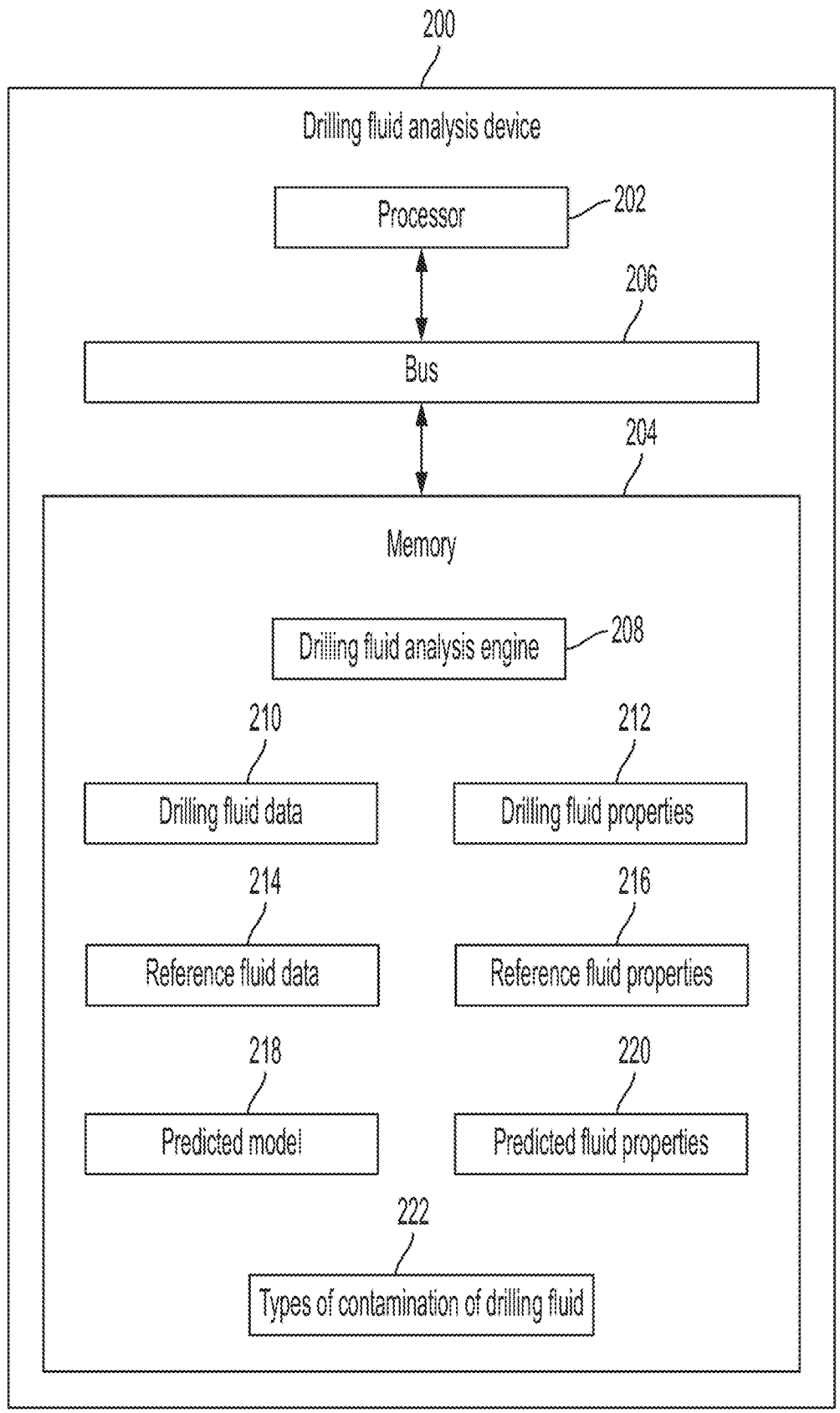
FIG. 2 is a block diagram of a drilling fluid analysis system for identifying a type of contamination of drilling fluid according to one example of the present disclosure.

FIG. 2 is a block diagram of a drilling fluid analysis device 200 for identifying a type of contamination of drilling fluid according to one example of the present disclosure. The drilling fluid analysis device 200 can include a processor 202, a bus 206, and a memory 204. In some examples, the components shown in FIG. 2 can be integrated into a single structure. For example, the components can be within a single housing with a single processing device. In other examples, the components shown in FIG. 2 can be distributed (e.g., in separate housings) and in electrical communication with each other using various processors. It is also possible for the components to be distributed in a cloud computing system or grid computing system.

The processor 202 can execute one or more operations for receiving real-time data and determining a caving volume prediction. The processor 202 can execute drilling fluid analysis engine stored in the memory 204 to perform the operations. The processor 202 can include one processing device or multiple processing devices. Examples of the processor 202 can include a field-programmable gate array ("FPGA"), an application-specific integrated circuit ("ASIC"), a processor, a microprocessor, etc.

The processor 202 is communicatively coupled to the memory 204 via the bus 206. The memory 204 may include any type of memory device that retains stored information when powered off. Examples of the memory 204 can include electrically erasable and programmable read-only memory ("EEPROM"), flash memory, or any other type of non-volatile memory. In some examples, at least some of the memory 204 can include a non-transitory medium from which the processor 202 can read drilling fluid analysis engine 208. A computer-readable medium can include electronic, optical, magnetic, or other storage devices capable of providing the processor 202 with computer-readable drilling fluid analysis engine or other program code. Non-limiting examples of a computer-readable medium include (but are not limited to) magnetic disk(s), memory chip(s), read-only memory (ROM), random-access memory ("RAM"), an ASIC, a configured processing device, optical storage, or any other medium from which a computer processing device can read drilling fluid analysis engine. The drilling fluid analysis engine 208 can include processing device-specific drilling fluid analysis engine generated by a compiler or an interpreter from code written in any suitable computer-programming language, including, for example, C, C++, C#, etc.

The processor 202 may execute the drilling fluid analysis engine 208 to determine a caving volume prediction based on real-time data. For example, the processor 202 may receive drilling fluid data 210. The drilling fluid data can be measured in real time, such as from the sensor 122. The processor 202 may also receive reference drilling fluid data 210 for use in determining a predicted model related to types of contamination of drilling fluid 222. The processor 202 may determine properties of drilling fluid 212 using drilling fluid data 210. The processor 202 may determine reference fluid properties 216 using the reference fluid data 214. The processor 202 can determine a predicted model 218 using fluid properties of drilling fluid 212 and reference fluid properties 216. For example, the processor 202 may determine the predicted model 218 using the difference between fluid properties of drilling fluid 212 and reference fluid properties 216. The processor 202 can determine predicted fluid properties 220 using predicted model 218. The processor 202 can determine one of types of contamination of drilling fluid 222 using a difference between properties of drilling fluid 212 and predicted fluid properties 220.

Figure 3:
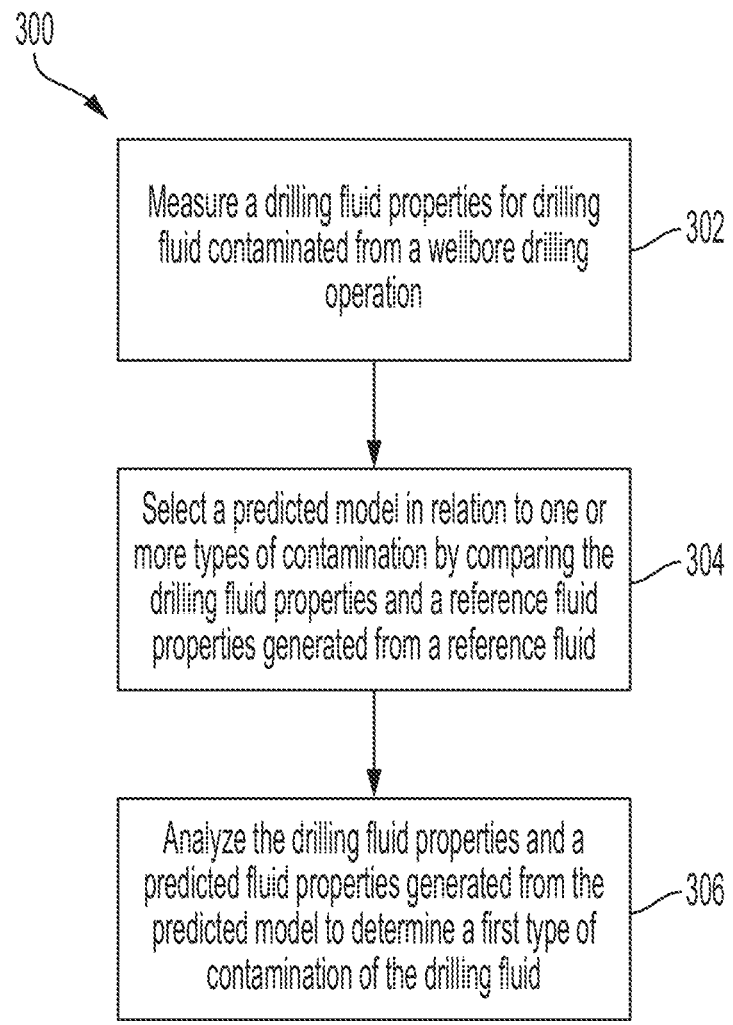
FIG. 3 is a flow chart of a process to identify a type of contamination of drilling fluid according to one example of the present disclosure.

FIG. 3 is a flow chart of a process 300 to identify a type of contamination of drilling fluid according to one example of the present disclosure. In some examples, the drilling fluid analysis device 126 in the drilling system can receive the drilling fluid surrounding the drilling rig 100 or drilling fluid from the subterranean formation 101. At block 302, in some examples, the drilling fluid analysis device 126 can receive drilling fluid prior to pumping into wellbore through drilling bit. In some examples, the drilling fluid analysis device 126 can measure drilling fluid properties from drilling fluid, which may be contaminated from a wellbore drilling operation. Examples of contamination types of drilling fluid 222 can include oil, Brine, low gravity solid (LGS), high gravity solid (HGS) in drilling fluid. Examples of drilling fluid properties can include mud weight (MW), thermal conductivity (TC), density, and salinity in drilling fluid, which may be contaminated during the drilling operation.

At block 304, the processor 202 can select a predicted model in relation to one or more types of contamination by comparing the drilling fluid and reference fluid properties generated from a reference fluid. In some examples, the reference fluid drilling can be stored in the memory 204 as reference fluid data 214. The processor 202 can determine reference fluid properties using the reference drilling fluid. Examples of reference fluid properties can include mud weight (MW), thermal conductivity (TC), density, and salinity in reference fluid. In some examples, the processor 202 can select a predicted model in relation to one or more types of contamination based on a difference between drilling fluid properties and reference fluid properties. Examples of a predicted model can be related to one or more types of contamination, including include oil, Brine, low gravity solid (LGS), high gravity solid (HGS).

In some examples, the difference between drilling fluid properties and reference fluid properties can be estimated in quantitative value. Some aspects of estimating difference between drilling fluid properties and reference fluid properties in their mud weight (MW) can be calculated by the following equation (1):

$$MW - MW_{ref} = \Sigma \Delta V_i^* \rho_i \qquad (1)$$

Wherein the MW can be mud weight in drilling fluid, $MW_{ref}$ can be mud weight in reference fluid. i can be a sample number of drilling fluid samples in sequences of drilling fluid. $\Delta V_i$ can be fluid volume change in between a drilling fluid sample and a reference fluid sample at a particular density $\rho_i$. In some examples, the processor 202 can summarize each drilling fluid sample i by multiplying $\Delta V_i$ and $\rho_i$ to calculate an estimated difference of mud weights between drilling fluid and reference fluid.

In some examples, the difference between drilling fluid properties and reference fluid properties can be estimated in quantitative value. Some aspects of estimating difference between drilling fluid properties and reference fluid properties in their thermal conductivity (TC) can be calculated by the following equation (2):

$$TC-TC_{ref}=\Sigma f(TC_i, V_i) \qquad (2)$$

Wherein the TC can be thermal conductivity in drilling fluid, $TC_{ref}$ can be thermal conductivity in reference fluid. i can be a sample number of drilling fluid samples in sequences of drilling fluid. $TC_i$, can be thermal conductivity of a drilling fluid sample i. $V_i$ can be drilling fluid volume in a drilling fluid sample i. $f$ can be a mathematical function. For example, $f$ can be a function of weighting values of $TC_i$, and $V_i$ by multiplying them with an integer or a number between 0 to 1. In some examples, the processor 202 can summarize each drilling fluid sample i to calculate an estimated difference of thermal conductivities between drilling fluid and reference fluid.

At block 306, the processor 202 can analyze the drilling fluid properties and predicted fluid properties generated from the predicted model to determine a first type of contamination of the drilling fluid. The first type of contamination can be one of types of contamination, including oil, Brine, low gravity solid (LGS), high gravity solid (HGS). Referring to block 304, the processor 202 can generate predicted fluid properties using a selected predicted model related to a particular type of contamination of drilling fluid. For example, the processor 202 can generate a predicted fluid properties based on a LGS type of predicted model for comparing to drilling fluid properties of drilling fluid. In another example, the processor 202 can generate predicted fluid properties based on a difference between drilling fluid properties and reference fluid properties through the equation (1) and (2). In some examples, the processor 202 can determine a first type of contamination of drilling fluid based on a difference between drilling fluid properties and predicted fluid properties. In some aspects, the calculation of the difference between drilling fluid properties and predicted fluid properties can be the similar rationale as calculation difference between drilling fluid properties and reference fluid properties.

Figure 4:
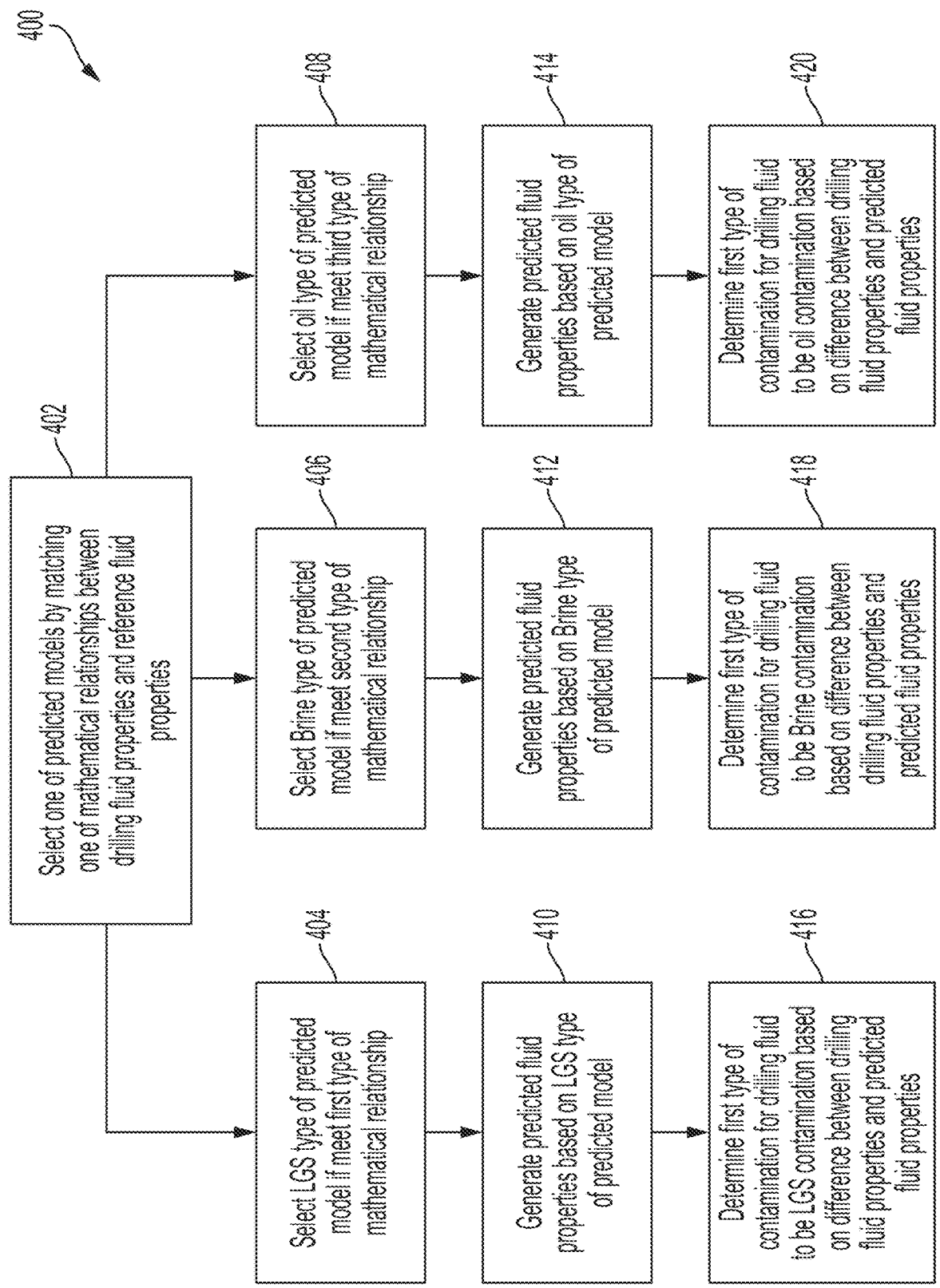
FIG. 4 is a flow chart of a process to identify first type of contamination in drilling fluid according to one example of the present disclosure.

FIG. 4 is a flow chart of a process 400 to identify first type contaminants in drilling fluid according to one example of the present disclosure. At block 402, the processor 202 can select one of predicted models by matching one of mathematical relationships between drilling fluid properties and reference fluid properties. The predicted models can be related to one of types of contamination in drilling fluid, such as oil, Brine, low gravity solid (LGS), high gravity solid (HGS). In some examples, the mathematical relationships can be a result of comparison between drilling fluid properties and reference fluid properties.

At block 404, the processor 202 can select LGS type of predicted model if a result of comparison between drilling fluid properties and reference fluid properties in their mud weight (MW) and thermal conductivity (TC) meets by following first type of mathematical relationship (M1).

$$MW>MW_{ref}TC \geq TC_{ref} \qquad (M1)$$

When mud weight of drilling fluid is larger than mud weight of reference fluid, and thermal conductivity of drilling fluid is at least equal to thermal conductivity of reference fluid, then the processor 202 can determine the result of comparison between drilling fluid properties and reference fluid properties meets mathematical relationship (M1) and select LGS type of predicted model for drilling fluid in use of determination a type of contamination.

At block 410, the processor 202 can generate predicted fluid properties based on LGS type of predicted model. In some examples, LGS type of predicted model can be stored in memory 204 along with corresponding reference fluid properties 216, for example, fluid properties in LGS type of contamination.

At block 416, the processor 202 can determine first type of contamination for drilling fluid to be LGS contamination based on a difference between drilling fluid properties and predicted fluid properties. In some examples, the processor 202 can calculate a difference between drilling fluid properties and predicted fluid properties through equations (1) and (2). In some examples, the processor 202 can determine first type of contamination for drilling fluid to be LGS contamination using first predetermined error. For example, the first type of contamination can be determined to LGS contamination based on a difference between thermal conductivity of drilling fluid properties and thermal conductivity of predicted fluid properties using first predetermined error by following first determined condition (D1):

$$|TC^a-TC^p|>A \qquad (D1)$$

Wherein the $TC^a$ can be an actual measurement of thermal conductivity of drilling fluid which measured by the drilling fluid analysis device 200, $TC^p$ can be a predicted measurement of thermal conductivity generated based on a predicted model related to LGS type of contamination. The difference between thermal conductivities can be calculated by processor 202 and may have similar rationale referring to equation (2). A can be a first predetermined error, which may be an instrumental error, for example. If the absolute value of the difference between $TC^a$ and $TC^p$ is larger than A, the first predetermined error, then a further determination may be needed for determining a second type of contamination of drilling fluid respect with FIG. 5. Otherwise, the processor 202 can determine LGS type of contamination in drilling fluid.

In a particular example, If the absolute value of the difference between $TC^a$ and $TC^p$ is larger than A, the predicted model related to LGS type of contamination may change to a predicted model related to HGS type of contamination. And, the processor 202 may be referring back to block 410 and 416 to determine the first type of contamination for drilling fluid using the predicted model related to HGS type of contamination.

At block 406, the processor 202 can select Brine type of predicted model if a result of comparison between drilling fluid properties and reference fluid properties in their mud weight (MW) and thermal conductivity (TC) meets by following first type of mathematical relationship (M2).

$$MW \leq MW_{ref}TC>TC_{ref} \qquad (M2)$$

When mud weight of drilling fluid is at most equal to mud weight of reference fluid and thermal conductivity of drilling fluid is larger than thermal conductivity of reference fluid, then the processor 202 can determine the result of comparison between drilling fluid properties and reference fluid properties meets mathematical relationship (M2) and select Brine type of predicted model for drilling fluid in use of determination a type of contamination.

At block 412, the processor 202 can generate predicted fluid properties based on Brine type of predicted model and may have a similar rationale to block 410.

At block 418, the processor 202 can determine first type of contamination for drilling fluid to be Brine contamination based on a difference between drilling fluid properties and predicted fluid properties and may have a similar rationale to block 416.

At block 408, the processor 202 can select oil type of predicted model if a result of comparison between drilling fluid properties and reference fluid properties in their mud weight (MW) and thermal conductivity (TC) meets by following first type of mathematical relationship (M3).

$$MW \le MW_{ref}, TC \le TC_{ref} \quad \text{(M3)}$$

When mud weight of drilling fluid is larger than mud weight of reference fluid and thermal conductivity of drilling fluid is at least equal to thermal conductivity of reference fluid, then the processor 202 can determine the result of comparison between drilling fluid properties and reference fluid properties. If the result meets mathematical relationship (M3), then select oil type of predicted model for drilling fluid in use of determination a type of contamination.

At block 414, the processor 202 can generate predicted fluid properties based on oil type of predicted model and may have a similar rationale to block 410 and 412.

At block 420, the processor 202 can determine first type of contamination for drilling fluid to be oil contamination based on a difference between drilling fluid properties and predicted fluid properties and may have a similar rationale to block 416 and 418.

Figure 5:
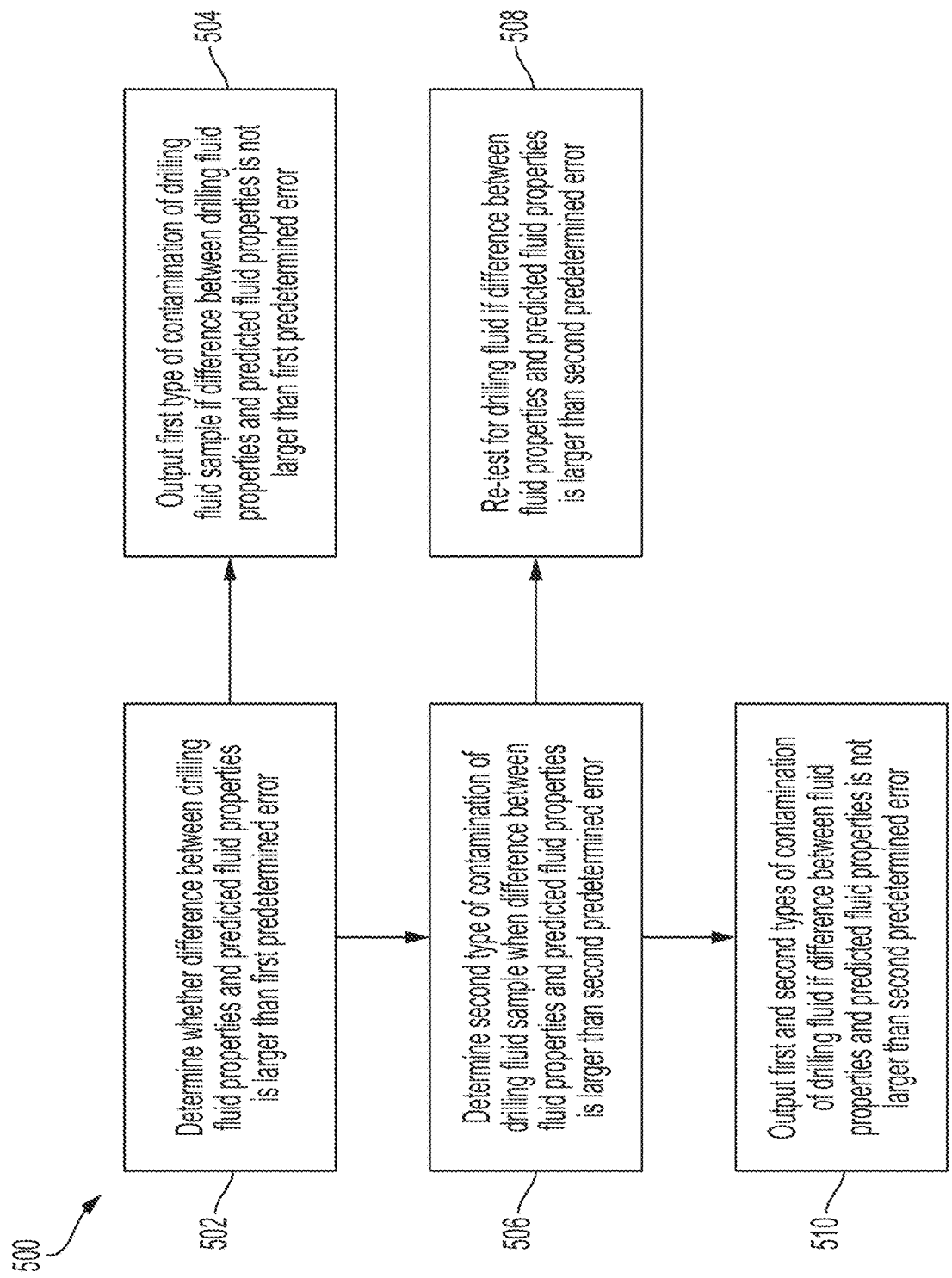
FIG. 5 is a flow chart of a process to identify first and second types of contamination in drilling fluid according to one example of the present disclosure.

FIG. 5 is a flow chart of a process 500 to identify first and second types of contaminants in drilling fluid according to one example of the present disclosure. At block 502, the processor 202 can determine whether the difference between drilling fluid properties and predicted fluid properties is larger than first predetermined error. In some aspects, if the difference is larger than first predetermined error, then processor 202 may proceed to block 506. Otherwise, the processor 202 may proceed to block 504.

At block 504, referring to block 416, 418, and 420, the processor 202 may output first type of contamination of drilling fluid sample if difference between drilling fluid properties and predicted fluid properties is not larger than first predetermined error.

In one example, the first type of contamination of drilling fluid sample can be used to predict a concentration of drilling fluid suitable for use in downhole during drilling operations. A suitable concentration of drilling fluid can be determined by analyzing the drilling fluid sample in response to the first type of contamination. In other examples, some materials can be added into the drilling fluid based on the drilling fluid sample that includes the first type of contamination. For example, viscosity decreaser, viscosity increaser, or water can be employed as materials and added into the drilling fluid in response to the first type of contamination. By doing this, the suitable concentration of drilling fluid can be obtained for use in drilling operations.

In the other example, the first type of contamination of drilling fluid sample can be used to facilitate the drilling operation or other operations in a downhole by analyzing a possible pressure in the wellbore related to the first type of contamination. The possible pressure in the wellbore can be determined by analyzing the drilling fluid sample that includes the first type of contamination. For example, one or more contaminated compositions in the drilling fluid sample may tend to reduce hydrostatic pressure in the wellbore during the drilling operation. Thus, the drilling operation may be needed to be performed in response to the lower hydrostatic pressure in the downhole.

At block 506, the processor 202 can determine second type of contamination of drilling fluid sample when difference between fluid properties and predicted fluid properties is larger than second predetermined error. In some examples, the processor 202 can determine second type of contamination based on a difference between drilling fluid properties and predicted fluid properties in mud weight and thermal conductivity by following determination condition (D2):

$$|TC^a - TC^p| > B, |MW^a - MW^p| > B \quad \text{(D2)}$$

Wherein the $MW^a$ can be an actual measurement of mud weight of drilling fluid which measured by the drilling fluid analysis device 200, $MW^p$ can be a predicted measurement of mud weight generated based on a predicted model related to a type of contamination. The difference between mud weights can be calculated by processor 202 and may have similar rationale referring to equation (1). The $TC^a$ can be an actual measurement of thermal conductivity of drilling fluid which measured by the drilling fluid analysis device 200, $TC^p$ can be a predicted measurement of thermal conductivity generated based on a predicted model related to a type of contamination. The difference between thermal conductivities can be calculated by processor 202 and may have similar rationale referring to equation (2). B can be a second predetermined error, which may be an instrumental error, for example. If the absolute value of the difference between $MW^a$ and $MW^p$ is larger than B and the difference between $TC^a$ and $TC^p$ is larger than B, then the processor 202 may need to re-test for drilling at block 508. Otherwise, the processor 202 can output first and second types of contamination of drilling fluid if differences between fluid properties and predicted fluid properties are not larger than second predetermined error at block 510.

In one example, the first and second types of contamination of drilling fluid sample can be used to predict a concentration of drilling fluid suitable for use in downhole during drilling operations. A suitable concentration of drilling fluid can be determined by analyzing the drilling fluid sample in response to the first and second types of contamination. In other examples, some materials can be added into the drilling fluid based on the drilling fluid sample that includes the first and second types of contamination. For example, viscosity decreaser, viscosity increaser, or water can be employed as materials and added into the drilling fluid in response to the first and second types of contamination. By doing this, the suitable concentration of drilling fluid can be obtained for use in drilling operations.

In the other example, the first and second types of contamination of drilling fluid sample can be used to facilitate the drilling operation or other operations in a downhole by analyzing a possible pressure in the wellbore related to the first and second types of contamination. The possible pressure in the wellbore can be determined by analyzing the drilling fluid sample that includes the first and second types of contamination. For example, one or more contaminated compositions in the drilling fluid sample may tend to reduce hydrostatic pressure in the wellbore during the drilling operation. Thus, the drilling operation may be needed to be performed in response to the lower hydrostatic pressure in the downhole.

In some aspects, one or more types of contamination of the drilling fluid can be identified for drilling operation. As used below, any reference to a series of examples is to be understood as reference to each of those examples disjunctively (E.g., "Examples 1-4" is to be understood as Examples 1, 2, 3, or 4").

Example 1 is a system comprising: a processor; and a non-transitory computer-readable medium comprising instructions that are executable by the processor to cause the processor to perform operations comprising: measuring a first plurality of fluid properties for a drilling fluid sample contaminated from a wellbore drilling operation; selecting a predicted model in relation to one or more types of contamination by comparing the first plurality of fluid properties and a second plurality of fluid properties measured from a reference fluid sample; and analyzing the first plurality of fluid properties and a third plurality of fluid properties generated from the predicted model to determine a first type of contamination in the drilling fluid sample. Example #2: The system of Example #1 may includes Example 2 is the system of example 1, wherein the first, the second, and the third plurality of fluid properties include a thermal conductivity in a fluid sample, mud weight in a fluid sample, density in a fluid sample, and salinity in a fluid sample.

Example 3 is the system of example 1, wherein the operations further comprise selecting the predicted model according to a mathematical relationship between at least one property of the first plurality of fluid properties and at least one property of the second plurality of fluid properties.

Example 4 is the system of example 1, wherein the operations further comprise analyzing at least one of the first plurality of fluid properties and at least one of the third plurality of fluid properties to determine the first type of contamination in the drilling fluid sample based on a first difference with a first predetermined error between at least one of the first plurality of fluid properties and at least one of the third plurality of fluid properties, wherein the first type of contamination in the drilling fluid is usable for determining a concentration of the drilling fluid, a material for adding into the drilling fluid, or viscosity of the drilling fluid.

Example 5 is the system of example 4, wherein the operations further comprise analyzing at least two of the first plurality of fluid properties and at least two of the third plurality of fluid properties to determine a second type of contamination in the drilling fluid sample based on a second difference with a second predetermined error between at least two of the first plurality of fluid properties and at least two of the third plurality of fluid properties, wherein the first difference is larger than a first predetermined error, and wherein the first and second types of contamination in the drilling fluid is usable for determining a concentration of the drilling fluid, a material for adding into the drilling fluid, or viscosity of the drilling fluid.

Example 6 is the system of example(s) 4, wherein the predicted model is a first predicted model, and wherein the operations further comprise selecting a second predicted model based on the first difference, wherein the first difference is larger than the first predetermined error.

Example 7 is the system of example 6, wherein the operations further comprise analyzing the first plurality of fluid properties and the third plurality of fluid properties generated from the second predicted model to determine the first type of contamination in the drilling fluid sample.

Example 8 is a method comprising: measuring a first plurality of fluid properties for a drilling fluid sample contaminated from a wellbore drilling operation; selecting a predicted model in relation to one or more types of contamination by comparing the first plurality of fluid properties and a second plurality of fluid properties measured from a reference fluid sample; and analyzing the first plurality of fluid properties and a third plurality of fluid properties generated from the predicted model to determine a first type of contamination in the drilling fluid sample.

Example 9 is the method of example 8, wherein the first, the second, and the third plurality of fluid properties include a thermal conductivity in a fluid sample, mud weight in a fluid sample, density in a fluid sample, and salinity in a fluid sample.

Example 10 is the method of example 8, further comprising selecting the predicted model according to a mathematical relationship between at least one property of the first plurality of fluid properties and at least one property of the second plurality of fluid properties.

Example 11 is the method of example 8, further comprising analyzing at least one of the first plurality of fluid properties and at least one of the third plurality of fluid properties to determine the first type of contamination in the drilling fluid sample based on a first difference with a first predetermined error between at least one of the first plurality of fluid properties and at least one of the third plurality of fluid properties, wherein the first type of contamination in the drilling fluid is used for determining a concentration of the drilling fluid, a material for adding into the drilling fluid, or viscosity of the drilling fluid.

Example 12 is the method of example 11, further comprising analyzing at least two of the first plurality of fluid properties and at least two of the third plurality of fluid properties to determine a second type of contamination in the drilling fluid sample based on a second difference with a second predetermined error between at least two of the first plurality of fluid properties and at least two of the third plurality of fluid properties, wherein the first difference is larger than a first predetermined error, and wherein the first and second types of contamination in the drilling fluid are used for determining a concentration of the drilling fluid, a material for adding into the drilling fluid, or viscosity of the drilling fluid.

Example 13 is the method of example 11, wherein the predicted model is a first predicted model, and further comprising selecting a second predicted model based on the first difference, wherein the first difference is larger than the first predetermined error.

Example 14 is the method of example 13, further comprising analyzing the first plurality of fluid properties and the third plurality of fluid properties generated from the second predicted model to determine the first type of contamination in the drilling fluid sample.

Example 15 is a non-transitory computer-readable medium comprising instructions that are executable by a processing device for causing the processing device to perform operations comprising: measuring a first plurality of fluid properties for a drilling fluid sample contaminated from a wellbore drilling operation; selecting a predicted model in relation to one or more types of contamination by comparing the first plurality of fluid properties and a second plurality of fluid properties measured from a reference fluid sample; and analyzing the first plurality of fluid properties and a third plurality of fluid properties generated from the predicted model to determine a first type of contamination in the drilling fluid sample.

Example 16 is the non-transitory computer-readable medium of example 15, wherein the first, the second, and the third plurality of fluid properties include a thermal conductivity in a fluid sample, mud weight in a fluid sample, density in a fluid sample, and salinity in a fluid sample.

Example 17 is the non-transitory computer-readable medium of example 15, wherein the operations further comprise selecting the predicted model according to a mathematical relationship between at least one property of the first plurality of fluid properties and at least one property of the second plurality of fluid properties.

Example 18 is the non-transitory computer-readable medium of example 15, wherein the operations further comprise analyzing at least one of the first plurality of fluid properties and at least one of the third plurality of fluid properties to determine the first type of contamination in the drilling fluid sample based on a first difference with a first predetermined error between at least one of the first plurality of fluid properties and at least one of the third plurality of fluid properties, wherein the first type of contamination in the drilling fluid is usable for determining a concentration of the drilling fluid, a material for adding into the drilling fluid, or viscosity of the drilling fluid.

Example 19 is the non-transitory computer-readable medium of example 18, wherein the operations further comprise analyzing at least two of the first plurality of fluid properties and at least two of the third plurality of fluid properties to determine a second type of contamination in the drilling fluid sample based on a second difference with a second predetermined error between at least two of the first plurality of fluid properties and at least two of the third plurality of fluid properties, wherein the first difference is larger than a first predetermined error, and wherein the first and second types of contamination in the drilling fluid are usable for determining a concentration of the drilling fluid, a material for adding into the drilling fluid, or viscosity of the drilling fluid.

Example 20 is the non-transitory computer-readable medium of example 18, wherein the predicted model is a first predicted model, and further comprising selecting a second predicted model based on the first difference, wherein the first difference is larger than the first predetermined error.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A system comprising:
   a processor; and
   a non-transitory computer-readable medium comprising instructions that are executable by the processor to cause the processor to perform operations comprising:
   measuring a first plurality of fluid properties for a drilling fluid sample contaminated from a wellbore drilling operation;
   selecting a predicted model in relation to one or more types of contamination based on comparing the first plurality of fluid properties and a second plurality of fluid properties measured from a reference fluid sample;
   analyzing, using the predicted model, the first plurality of fluid properties and a third plurality of fluid properties generated from the predicted model to determine a first type of contamination in the drilling fluid sample based on a first difference with a first predetermined error between the first plurality of fluid properties and the third plurality of fluid properties;
   analyzing the first plurality of fluid properties and the third plurality of fluid properties to determine a second type of contamination in the drilling fluid sample based on a second difference with a second predetermined error between the first plurality of fluid properties and the third plurality of fluid properties; and
   outputting, based on the first type of contamination in the drilling fluid sample and the second type of contamination in the drilling fluid sample, a command for controlling the wellbore drilling operation by adding materials to a drilling fluid and adjusting hydrostatic pressure.

2. The system of claim 1, wherein the first plurality of fluid properties, the second plurality of fluid properties, and the third plurality of fluid properties include a thermal conductivity in a fluid sample, mud weight in a fluid sample, density in a fluid sample, and salinity in a fluid sample.

3. The system of claim 2, wherein the operation of analyzing, using the predicted model, the first plurality of fluid properties and the third plurality of fluid properties generated from the predicted model to determine the first type of contamination in the drilling fluid sample based on the first difference with the first predetermined error between the first plurality of fluid properties and the third plurality of fluid properties comprises:
   analyzing the thermal conductivity of the first plurality of fluid properties and the thermal conductivity of the third plurality of fluid properties; and
   determining the first type of contamination in the drilling fluid sample based on the first difference with the first predetermined error between the thermal conductivity of the first plurality of fluid properties and the thermal conductivity of the third plurality of fluid properties, wherein the first type of contamination in the drilling fluid sample is usable for determining a concentration of the drilling fluid, a material for adding into the drilling fluid, or viscosity of the drilling fluid as the command to control the wellbore drilling operation.

4. The system of claim 3, wherein the predicted model is a first predicted model, and wherein the operations further comprise selecting a second predicted model based on the first difference, wherein the first difference is larger than the first predetermined error.

5. The system of claim 4, wherein the operations further comprise analyzing the first plurality of fluid properties and the third plurality of fluid properties generated from the second predicted model to determine the first type of contamination in the drilling fluid sample.

6. The system of claim 1, wherein the operations further comprise selecting the predicted model according to a mathematical relationship between at least one property of the first plurality of fluid properties and at least one property of the second plurality of fluid properties.

7. The system of claim 2, wherein the operation of analyzing the first plurality of fluid properties and the third plurality of fluid properties to determine the second type of contamination in the drilling fluid sample based on the second difference with the second predetermined error between the first plurality of fluid properties and the third plurality of fluid properties comprises:
   analyzing the thermal conductivity and the mud weight of the first plurality of fluid properties and the thermal conductivity and the mud weight of the third plurality of fluid properties; and
   determining the second type of contamination in the drilling fluid sample based on the second difference with the second predetermined error between the thermal conductivity and the mud weight of the first plurality of fluid properties and the thermal conductivity and the mud weight of the third plurality of fluid properties, wherein the first difference is larger than a first predetermined error, and wherein the first and second types of contamination in the drilling fluid sample is usable for determining a concentration of the drilling fluid, a material for adding into the drilling fluid, or viscosity of the drilling fluid as the command to control the wellbore drilling operation.

8. A method comprising:
measuring a first plurality of fluid properties for a drilling fluid sample contaminated from a wellbore drilling operation;
selecting a predicted model in relation to one or more types of contamination based on comparing the first plurality of fluid properties and a second plurality of fluid properties measured from a reference fluid sample;
analyzing, using the predicted model, the first plurality of fluid properties and a third plurality of fluid properties generated from the predicted model to determine a first type of contamination in the drilling fluid sample based on a first difference with a first predetermined error between the first plurality of fluid properties and the third plurality of fluid properties;
analyzing the first plurality of fluid properties and the third plurality of fluid properties to determine a second type of contamination in the drilling fluid sample based on a second difference with a second predetermined error between the first plurality of fluid properties and the third plurality of fluid properties; and
outputting, based on the first type of contamination in the drilling fluid sample and the second type of contamination in the drilling fluid sample, a command for controlling the wellbore drilling operation by adding materials to a drilling fluid and adjusting hydrostatic pressure.

9. The method of claim 8, wherein the first plurality of fluid properties, the second plurality of fluid properties, and the third plurality of fluid properties include a thermal conductivity in a fluid sample, mud weight in a fluid sample, density in a fluid sample, and salinity in a fluid sample.

10. The method of claim 9, where the analyzing, using the predicted model, the first plurality of fluid properties and the third plurality of fluid properties generated from the predicted model to determine the first type of contamination in the drilling fluid sample based on the first difference with the first predetermined error between the first plurality of fluid properties and the third plurality of fluid properties comprises:
analyzing the thermal conductivity of the first plurality of fluid properties and the thermal conductivity of the third plurality of fluid properties; and
determining the first type of contamination in the drilling fluid sample based on the first difference with the first predetermined error between the thermal conductivity of the first plurality of fluid properties and the thermal conductivity of the third plurality of fluid properties, wherein the first type of contamination in the drilling fluid sample is usable for determining a concentration of the drilling fluid, a material for adding into the drilling fluid, or viscosity of the drilling fluid as the command to control the wellbore drilling operation.

11. The method of claim 10, wherein the predicted model is a first predicted model, and further comprising selecting a second predicted model based on the first difference, wherein the first difference is larger than the first predetermined error.

12. The method of claim 11, further comprising analyzing the first plurality of fluid properties and the third plurality of fluid properties generated from the second predicted model to determine the first type of contamination in the drilling fluid sample.

13. The method of claim 9, wherein the analyzing the first plurality of fluid properties and the third plurality of fluid properties to determine the second type of contamination in the drilling fluid sample based on the second difference with the second predetermined error between the first plurality of fluid properties and the third plurality of fluid properties comprises:
analyzing the thermal conductivity and the mud weight of the first plurality of fluid properties and the thermal conductivity and the mud weight of the third plurality of fluid properties; and
determining the second type of contamination in the drilling fluid sample based on the second difference with the second predetermined error between the thermal conductivity and the mud weight of the first plurality of fluid properties and the thermal conductivity and the mud weight of the third plurality of fluid properties, wherein the first difference is larger than a first predetermined error, and wherein the first and second types of contamination in the drilling fluid sample is usable for determining a concentration of the drilling fluid, a material for adding into the drilling fluid, or viscosity of the drilling fluid as the command to control the wellbore drilling operation.

14. The method of claim 8, further comprising selecting the predicted model according to a mathematical relationship between at least one property of the first plurality of fluid properties and at least one property of the second plurality of fluid properties.

15. A non-transitory computer-readable medium comprising instructions that are executable by a processing device for causing the processing device to perform operations comprising:
measuring a first plurality of fluid properties for a drilling fluid sample contaminated from a wellbore drilling operation;
selecting a predicted model in relation to one or more types of contamination based on comparing the first plurality of fluid properties and a second plurality of fluid properties measured from a reference fluid sample;
analyzing, using the predicted model, the first plurality of fluid properties and a third plurality of fluid properties generated from the predicted model to determine a first type of contamination in the drilling fluid sample based on a first difference with a first predetermined error between the first plurality of fluid properties and the third plurality of fluid properties;
analyzing the first plurality of fluid properties and the third plurality of fluid properties to determine a second type of contamination in the drilling fluid sample based on a second difference with a second predetermined error between the first plurality of fluid properties and the third plurality of fluid properties; and
outputting, based on the first type of contamination in the drilling fluid sample and the second type of contamination in the drilling fluid sample, a command for controlling the wellbore drilling operation by adding materials to a drilling fluid and adjusting hydrostatic pressure.

16. The non-transitory computer-readable medium of claim 15, wherein the first plurality of fluid properties, the second plurality of fluid properties, and the third plurality of fluid properties include a thermal conductivity in a fluid sample, mud weight in a fluid sample, density in a fluid sample, and salinity in a fluid sample.

17. The non-transitory computer-readable medium of claim 16, where the analyzing, using the predicted model, the first plurality of fluid properties and the third plurality of fluid properties generated from the predicted model to determine the first type of contamination in the drilling fluid sample based on the first difference with the first predetermined error between the first plurality of fluid properties and the third plurality of fluid properties comprises:

analyzing the thermal conductivity of the first plurality of fluid properties and the thermal conductivity of the third plurality of fluid properties; and determining the first type of contamination in the drilling fluid sample based on the first difference with the first predetermined error between the thermal conductivity of the first plurality of fluid properties and the thermal conductivity of the third plurality of fluid properties, wherein the first type of contamination in the drilling fluid sample is usable for determining a concentration of the drilling fluid, a material for adding into the drilling fluid, or viscosity of the drilling fluid as the command to control the wellbore drilling operation.

18. The non-transitory computer-readable medium of claim 17, wherein the predicted model is a first predicted model, and further comprising selecting a second predicted model based on the first difference, wherein the first difference is larger than the first predetermined error.

19. The non-transitory computer-readable medium of claim 16, wherein the analyzing the first plurality of fluid properties and the third plurality of fluid properties to determine the second type of contamination in the drilling fluid sample based on the second difference with the second predetermined error between the first plurality of fluid properties and the third plurality of fluid properties comprises:

analyzing the thermal conductivity and the mud weight of the first plurality of fluid properties and the thermal conductivity and the mud weight of the third plurality of fluid properties; and determining the second type of contamination in the drilling fluid sample based on the second difference with the second predetermined error between the thermal conductivity and the mud weight of the first plurality of fluid properties and the thermal conductivity and the mud weight of the third plurality of fluid properties, wherein the first difference is larger than a first predetermined error, and wherein the first and second types of contamination in the drilling fluid sample is usable for determining a concentration of the drilling fluid, a material for adding into the drilling fluid, or viscosity of the drilling fluid as the command to control the wellbore drilling operation.

20. The non-transitory computer-readable medium of claim 15, wherein the operations further comprise selecting the predicted model according to a mathematical relationship between at least one property of the first plurality of fluid properties and at least one property of the second plurality of fluid properties.

* * * * *